United States Patent
Spertell

(10) Patent No.: US 9,216,058 B2
(45) Date of Patent: *Dec. 22, 2015

(54) METHOD AND APPARATUS FOR TREATING SUBCUTANEOUS HISTOLOGICAL FEATURES

(71) Applicant: Miramar Labs, Inc., Santa Clara, CA (US)

(72) Inventor: Robert Bruce Spertell, Northridge, CA (US)

(73) Assignee: Miramar Labs, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,833

(22) Filed: Aug. 28, 2014

(65) Prior Publication Data

US 2014/0378959 A1 Dec. 25, 2014

Related U.S. Application Data

(60) Continuation of application No. 13/673,144, filed on Nov. 9, 2012, now Pat. No. 8,853,600, which is a continuation of application No. 13/280,032, filed on Oct. 24, 2011, now Pat. No. 8,367,959, which is a continuation of application No. 09/637,923, filed on Aug. 14, 2000, now Pat. No. 8,073,550, which is a division of application No. 08/904,175, filed on Jul. 31, 1997, now Pat. No. 6,104,959.

(51) Int. Cl.
*H05B 6/70* (2006.01)
*H05B 6/50* (2006.01)
*A61B 18/18* (2006.01)

(Continued)

(52) U.S. Cl.
CPC ............ *A61B 18/1815* (2013.01); *A61N 5/025* (2013.01); *A61N 5/04* (2013.01); *A61B 18/203* (2013.01); *A61B 2018/00005* (2013.01); *A61B 2018/00023* (2013.01); *A61B 2018/00035* (2013.01); *A61B 2018/00083* (2013.01); *A61B 2018/00452* (2013.01); *A61B 2018/00458* (2013.01); *A61B 2018/00791* (2013.01); *A61N 2005/007* (2013.01)

(58) Field of Classification Search
None
See application file for complete search history.

(56) References Cited

U.S. PATENT DOCUMENTS

| | | |
|---|---|---|
| 2,407,690 A | 9/1946 | Southworth |
| 3,307,553 A | 3/1967 | Liebner |

(Continued)

FOREIGN PATENT DOCUMENTS

| | | |
|---|---|---|
| EP | 0139607 B1 | 4/1990 |
| EP | 0370890 B1 | 11/1995 |

(Continued)

OTHER PUBLICATIONS

Acculis; Microwave Ablation for Healthcare Professionals; 2 pgs.; accessed Jun. 24, 2008; (http://www.acculis.com/mta).

(Continued)

*Primary Examiner* — Thor Campbell
(74) *Attorney, Agent, or Firm* — Shay Glen LLP

(57) ABSTRACT

A system and method for treating subcutaneous histological features without affecting adjacent tissues adversely employs microwave energy of selected power, frequency and duration to penetrate subcutaneous tissue and heat target areas with optimum doses to permanently affect the undesirable features. The frequency chosen preferentially interacts with the target as opposed to adjacent tissue, and the microwave energy is delivered as a short pulse causing minimal discomfort and side effects. By distributing microwave energy at the skin over an area and adjusting power and frequency, different conditions, such as hirsuitism and telangiectasia, can be effectively treated.

2 Claims, 8 Drawing Sheets

(51) Int. Cl.
*A61N 5/04* (2006.01)
*A61N 5/02* (2006.01)
A61B 18/00 (2006.01)
A61B 18/20 (2006.01)
A61N 5/00 (2006.01)

(56) References Cited

U.S. PATENT DOCUMENTS

| | | |
|---|---|---|
| 3,527,227 A | 9/1970 | Fritz |
| 3,693,623 A | 9/1972 | Harte et al. |
| 3,845,267 A | 10/1974 | Fitzmayer |
| 4,069,827 A | 1/1978 | Dominy |
| 4,095,602 A | 6/1978 | Leveen |
| 4,108,147 A | 8/1978 | Kantor |
| 4,140,130 A | 2/1979 | Storm, III |
| 4,174,713 A | 11/1979 | Mehl |
| 4,190,053 A | 2/1980 | Sterzer |
| 4,190,056 A | 2/1980 | Tapper et al. |
| 4,197,860 A | 4/1980 | Sterzer |
| 4,228,809 A | 10/1980 | Paglione |
| 4,375,220 A | 3/1983 | Matvias |
| 4,378,806 A | 4/1983 | Henley Cohn |
| 4,388,924 A | 6/1983 | Weissman et al. |
| 4,397,313 A | 8/1983 | Vaguine |
| 4,397,314 A | 8/1983 | Vaguine |
| 4,446,874 A | 5/1984 | Vaguine |
| 4,528,991 A | 7/1985 | Dittmar et al. |
| 4,589,424 A | 5/1986 | Vaguine |
| 4,597,379 A | 7/1986 | Kihn et al. |
| 4,614,191 A | 9/1986 | Perler |
| 4,617,926 A | 10/1986 | Sutton |
| 4,632,128 A | 12/1986 | Paglione et al. |
| 4,641,649 A | 2/1987 | Walinsky et al. |
| 4,669,475 A | 6/1987 | Turner |
| 4,672,980 A | 6/1987 | Turner |
| 4,690,156 A | 9/1987 | Kikuchi et al. |
| 4,702,262 A | 10/1987 | Andersen et al. |
| 4,744,372 A | 5/1988 | Kikuchi et al. |
| 4,747,416 A | 5/1988 | Kikuchi et al. |
| 4,800,899 A | 1/1989 | Elliott |
| 4,825,880 A | 5/1989 | Stauffer et al. |
| 4,841,989 A | 6/1989 | Kikuchi et al. |
| 4,841,990 A | 6/1989 | Kikuchi et al. |
| 4,860,752 A | 8/1989 | Turner |
| 4,881,543 A | 11/1989 | Trembly et al. |
| 4,891,483 A | 1/1990 | Kikuchi et al. |
| 4,945,912 A | 8/1990 | Langberg |
| 4,974,587 A | 12/1990 | Turner et al. |
| 5,059,192 A | 10/1991 | Zaias |
| 5,097,846 A | 3/1992 | Larsen |
| 5,101,836 A | 4/1992 | Lee |
| 5,107,832 A | 4/1992 | Guibert et al. |
| 5,143,063 A | 9/1992 | Fellner |
| 5,186,181 A | 2/1993 | Franconi et al. |
| 5,190,518 A | 3/1993 | Takasu |
| 5,198,776 A | 3/1993 | Carr |
| 5,226,907 A | 7/1993 | Tankovich |
| 5,234,004 A | 8/1993 | Hascoet et al. |
| 5,246,438 A | 9/1993 | Langberg |
| 5,272,301 A | 12/1993 | Finger et al. |
| 5,295,955 A | 3/1994 | Rosen et al. |
| 5,301,692 A | 4/1994 | Knowlton |
| 5,305,748 A | 4/1994 | Wilk |
| 5,315,994 A | 5/1994 | Guibert et al. |
| 5,316,000 A | 5/1994 | Chapelon et al. |
| 5,364,336 A | 11/1994 | Carr |
| 5,364,394 A | 11/1994 | Mehl |
| 5,383,917 A | 1/1995 | Desai et al. |
| 5,385,544 A | 1/1995 | Edwards et al. |
| 5,405,346 A | 4/1995 | Grundy et al. |
| 5,407,440 A | 4/1995 | Zinreich et al. |
| 5,409,484 A | 4/1995 | Erlich et al. |
| 5,421,819 A | 6/1995 | Edwards et al. |
| 5,425,728 A | 6/1995 | Tankovich |
| 5,431,650 A | 7/1995 | Cosmescu |
| 5,433,740 A | 7/1995 | Yamaguchi |
| 5,441,532 A | 8/1995 | Fenn |
| 5,443,487 A | 8/1995 | Guibert et al. |
| 5,462,521 A | 10/1995 | Brucker et al. |
| 5,474,071 A | 12/1995 | Chapelon et al. |
| 5,503,150 A | 4/1996 | Evans |
| 5,507,741 A | 4/1996 | L'Esperance, Jr. |
| 5,507,790 A | 4/1996 | Weiss |
| 5,509,929 A | 4/1996 | Hascoet et al. |
| 5,522,814 A | 6/1996 | Bernaz |
| 5,531,662 A | 7/1996 | Carr |
| 5,540,681 A | 7/1996 | Strul et al. |
| 5,549,639 A | 8/1996 | Ross |
| 5,553,612 A | 9/1996 | Lundback |
| 5,569,237 A | 10/1996 | Beckenstein |
| 5,571,154 A | 11/1996 | Ren |
| 5,575,789 A | 11/1996 | Bell et al. |
| 5,584,830 A | 12/1996 | Ladd et al. |
| 5,586,981 A | 12/1996 | Hu |
| 5,595,568 A | 1/1997 | Anderson et al. |
| 5,649,973 A | 7/1997 | Tierney et al. |
| 5,660,836 A | 8/1997 | Knowlton |
| 5,662,110 A | 9/1997 | Carr |
| 5,669,916 A | 9/1997 | Anderson |
| 5,674,219 A | 10/1997 | Monson et al. |
| 5,683,381 A | 11/1997 | Carr et al. |
| 5,683,382 A | 11/1997 | Lenihan et al. |
| 5,690,614 A | 11/1997 | Carr et al. |
| 5,707,403 A | 1/1998 | Grove et al. |
| 5,724,966 A | 3/1998 | Lundback |
| 5,733,269 A | 3/1998 | Fuisz |
| 5,735,844 A | 4/1998 | Anderson et al. |
| 5,742,392 A | 4/1998 | Anderson et al. |
| 5,743,899 A | 4/1998 | Zinreich |
| 5,755,753 A | 5/1998 | Knowlton |
| 5,769,879 A | 6/1998 | Richards et al. |
| 5,776,127 A | 7/1998 | Anderson et al. |
| 5,782,897 A | 7/1998 | Carr |
| 5,810,801 A | 9/1998 | Anderson et al. |
| 5,810,804 A | 9/1998 | Gough et al. |
| 5,814,996 A | 9/1998 | Winter |
| 5,824,023 A | 10/1998 | Anderson |
| 5,830,208 A | 11/1998 | Muller |
| 5,836,999 A | 11/1998 | Eckhouse et al. |
| 5,868,732 A | 2/1999 | Waldman et al. |
| 5,879,346 A | 3/1999 | Waldman et al. |
| 5,891,094 A | 4/1999 | Masterson et al. |
| 5,897,549 A | 4/1999 | Tankovich |
| 5,902,263 A | 5/1999 | Patterson et al. |
| 5,904,709 A | 5/1999 | Arndt et al. |
| 5,919,218 A | 7/1999 | Carr |
| 5,931,860 A | 8/1999 | Reid et al. |
| 5,949,845 A | 9/1999 | Sterzer |
| 5,971,982 A | 10/1999 | Betsill et al. |
| 5,979,454 A | 11/1999 | Anvari et al. |
| 5,983,124 A | 11/1999 | Carr |
| 5,983,900 A | 11/1999 | Clement et al. |
| 5,989,245 A | 11/1999 | Prescott |
| 6,015,404 A | 1/2000 | Altshuler et al. |
| 6,026,331 A | 2/2000 | Feldberg et al. |
| 6,050,990 A | 4/2000 | Tankovich et al. |
| 6,093,186 A | 7/2000 | Goble |
| 6,104,959 A | 8/2000 | Spertell |
| 6,106,514 A | 8/2000 | O'Donnell, Jr. |
| 6,129,696 A | 10/2000 | Sibalis |
| 6,162,218 A | 12/2000 | Elbrecht et al. |
| 6,171,301 B1 | 1/2001 | Nelson et al. |
| 6,175,768 B1 | 1/2001 | Arndt et al. |
| 6,197,020 B1 | 3/2001 | O'Donnell, Jr. |
| 6,208,903 B1 | 3/2001 | Richards et al. |
| 6,210,367 B1 | 4/2001 | Carr |
| 6,214,034 B1 | 4/2001 | Azar |
| 6,223,076 B1 | 4/2001 | Tapper |
| 6,241,753 B1 | 6/2001 | Knowlton |
| 6,264,652 B1 | 7/2001 | Eggers et al. |
| 6,273,884 B1 | 8/2001 | Altshuler et al. |
| 6,277,111 B1 | 8/2001 | Clement et al. |
| 6,277,116 B1 | 8/2001 | Utely et al. |
| 6,306,128 B1 | 10/2001 | Waldman et al. |

(56) References Cited

U.S. PATENT DOCUMENTS

| | | | |
|---|---|---|---|
| 6,334,074 | B1 | 12/2001 | Spertell |
| 6,350,276 | B1 | 2/2002 | Knowlton |
| 6,430,446 | B1 | 8/2002 | Knowlton |
| 6,443,946 | B2 | 9/2002 | Clement et al. |
| 6,461,378 | B1 | 10/2002 | Knowlton |
| 6,470,216 | B1 | 10/2002 | Knowlton |
| 6,475,211 | B2 | 11/2002 | Chess et al. |
| 6,508,813 | B1 | 1/2003 | Altshuler |
| 6,517,532 | B1 | 2/2003 | Altshuler et al. |
| 6,575,969 | B1 | 6/2003 | Rittman, III et al. |
| 6,682,501 | B1 | 1/2004 | Nelson et al. |
| 6,878,144 | B2 | 4/2005 | Altshuler et al. |
| 7,006,874 | B2 | 2/2006 | Knowlton et al. |
| 7,115,123 | B2 | 10/2006 | Knowlton et al. |
| 7,151,964 | B2 | 12/2006 | Desai et al. |
| 7,189,230 | B2 | 3/2007 | Knowlton |
| 7,204,832 | B2 | 4/2007 | Altshuler et al. |
| 7,229,436 | B2 | 6/2007 | Stern et al. |
| 7,247,155 | B2 | 7/2007 | Hoey et al. |
| 7,267,675 | B2 | 9/2007 | Stern et al. |
| 7,758,537 | B1 | 7/2010 | Brunell et al. |
| 8,073,550 | B1 | 12/2011 | Spertell |
| 8,367,959 | B2 | 2/2013 | Spertell |
| 8,401,668 | B2 | 3/2013 | Deem et al. |
| 8,406,894 | B2 | 3/2013 | Johnson et al. |
| 8,469,951 | B2 | 6/2013 | Ben-Haim et al. |
| 8,535,302 | B2 | 9/2013 | Ben-Haim et al. |
| 8,688,228 | B2 | 4/2014 | Johnson et al. |
| 8,825,176 | B2 | 9/2014 | Johnson et al. |
| 8,853,600 | B2 | 10/2014 | Spertell |
| 2001/0005775 | A1 | 6/2001 | Samson |
| 2001/0050083 | A1 | 12/2001 | Marchitto et al. |
| 2003/0130575 | A1 | 7/2003 | Desai |
| 2003/0212393 | A1 | 11/2003 | Knowlton et al. |
| 2003/0216728 | A1 | 11/2003 | Stern et al. |
| 2004/0000316 | A1 | 1/2004 | Knowlton et al. |
| 2004/0002705 | A1 | 1/2004 | Knowlton et al. |
| 2006/0206110 | A1 | 9/2006 | Knowlton et al. |
| 2008/0269851 | A1 | 10/2008 | Deem et al. |
| 2008/0294152 | A1 | 11/2008 | Altshuler et al. |
| 2010/0049178 | A1 | 2/2010 | Deem et al. |
| 2010/0114086 | A1 | 5/2010 | Deem et al. |
| 2010/0211059 | A1 | 8/2010 | Deem et al. |
| 2011/0040299 | A1 | 2/2011 | Kim et al. |
| 2011/0196365 | A1 | 8/2011 | Kim et al. |
| 2011/0313412 | A1 | 12/2011 | Kim et al. |
| 2013/0035680 | A1 | 2/2013 | Ben-Haim et al. |
| 2013/0150844 | A1 | 6/2013 | Deem et al. |
| 2014/0005645 | A1 | 1/2014 | Ben-Haim et al. |
| 2014/0180271 | A1 | 6/2014 | Johnson et al. |
| 2015/0148792 | A1 | 5/2015 | Kim et al. |

FOREIGN PATENT DOCUMENTS

| | | |
|---|---|---|
| JP | 61-364 A | 1/1986 |
| JP | 62-149347 | 9/1987 |
| JP | S-63177856 A | 7/1988 |
| JP | 07-503874 A | 4/1995 |
| JP | H09-239040 A | 9/1997 |
| WO | WO 89/02292 A1 | 3/1989 |
| WO | WO 92/07622 A1 | 5/1992 |
| WO | WO 96/23447 A1 | 8/1996 |
| WO | WO 96/41579 A1 | 12/1996 |
| WO | WO 2009/072108 A2 | 6/2009 |

OTHER PUBLICATIONS

Aesthera US—How it Works; 2 pgs.; accessed Jul. 8, 2008 (http://www.aesthera.com/go/aestheraUS/patients/how_it_works/index.cfm).

Ashby et al.; Cryosurgery for Axillary Hyperhidrosis; British Medical Journal Short Reports; London; pp. 1173-1174; Nov. 13, 1976.

Bioportfolio; Tenex Health Receives FDA clearance for innovative TX1} tissue removal system; 2 pgs.; release dated Mar. 9, 2011; printed on Jun. 18, 2012 from website (http://www.bioportfolio.com/news/article/519143/Tenex-Health-Receives-Fda-Clearance-For-Innovative-Tx1-Tissue-Removal-System.html).

Campbell et al.; Dielectric properties of female human breast tissue measured in vitro at 3.2 GHz; Phys. Med. Biol.; 37(1); pp. 193-210; Jan. 1992.

Diederich et al.; Pre-clinical Evaluation of a Microwave Planar Array Applicator for Superficial Hyperthermia; International Journal of Hyperthermia; vol. 9, No. 2; pp. 227-246; Jan. 1993.

Duparc et al.; Anatomical basis of the variable aspects of injuries of the axillary nerve (excluding the terminal branches in the deltoid muscle); Surg Radiol Anat; vol. 19(3); pp. 127-132; May 1997.

Gabriel et al.; The dielectric properties of biological tissues: I. Literature survey; Phys Med Biol; 41(11); pp. 2231-2249; Nov. 1996.

Gabriel et al.; The dielectric properties of biological tissues: II. Measurements in the frequency range 10 Hz to 20 GHz; Phys Med Biol; 41(11); pp. 2251-2269; Nov. 1996.

Gabriel et al.; The dielectric properties of biological tissues: III. Parametric models for the dielectric spectrum of tissues; Phys Med Biol; 41(11); pp. 2271-2293; Nov. 1996.

Gabriel, et al.; Comparison of the Dielectric Properties of Normal and Wounded Human Skin Material; Bioelectromagnetics; 8; pp. 23-27; Jan. 1987.

Gabriel; Compilation of the dielectric properties of body tissues at RF and microwave frequencies (Technical Report); Armstrong Laboratory; Doc. No. AL/OE-TR-1996-004; pp. 1-16; Jan. 1996.

Gandhi et al.; Electromagnetic Absorption in the Human Head and Neck for Mobile Telephones at 835 and 1900 MHz; IEEE Transactions on Microwave Theory and Techniques; 44(10); pp. 1884-1897; Oct. 1996.

Gandhi et al.; Electromagnetic Absorption in the Human Head from Experimental 6-GHz Handheld Transceivers; IEEE Trans. on Electromagnetic Compatibility; 37(4); pp. 547-558; Nov. 1995.

Garber, B. B.; Office microwave treatment of enlarged prostate symptoms; 2 pgs.; printed from website (http://www.garber-online.com/microwave-treatment.htm) on Jun. 18, 2012.

Guidant Corp.; Guidant microwave surgical ablation system; 1 pg.; © 2004; printed Jun. 18, 2012 from website (http://web.archive.org/web/20070306031424/http://www.ctsnet.org/file/vendors/872/pdf/MicrowaveAblationIFU.pdf).

Guy, Arthur; History of Biological Effects and Medical Applications of Microwave Energy; IEEE Transactions on Microwave Theory and Techniques; 32(9); pp. 1182-1200; Sep. 1984.

Guy, Arthur; Therapeutic Heat and Cold, Fourth Ed.; Chapter 5: Biophysics of High-Frequency Currents and Electromagnetic Radiation; pp. 179-236. Williams and Wilkins (publishers); Apr. 1990.

Guy; Analyses of electromagnetic fields induced in biological tissues by thermographic studies on equivalent phantom models; IEEE Trans on Microwave Theory and Techniques; MTT-19(2); pp. 205-214; Feb. 1971.

Hey-Shipton, et al.; The Complex Permittivity of Human Tissue at Microwave Frequencies; Phys. Med. Biol.; 27(8); pp. 1067-1071; Aug. 1982.

Hisada et al.; Hereditary Hemorrhagic Telangiectasia Showing Severe Anemia which was successfully treated with estrogen; International Medicine; vol. 34; No. 6; pp. 589-592; Jun. 1995.

Kobayashi, T.; Electrosurgery Using Insulated Needles: Treatment of Axillary Bromhidrosis and Hyperhidrosis; Journal of Dermatologic Surgery & Oncology; 14(7) pp. 749-752; Jul. 1988.

Krusen, Frank (M.D.); Samuel Hyde Memorial Lecture: Medical Applications of Microwave Diathermy: Laboratory and Clinical Studies. Proceedings of the Royal Society of Medicine; 43(8); pp. 641-658, May 10, 1950.

Lagendijk et al; Hyperthermia dough: a fat and bone equivalent phantom to test microwave/radiofrequency hyperthermia heating systems; Phys. Med. Biol.; 30(7); pp. 709-712; Jul. 1985.

Land et al.; A quick accurate method for measuring the microwave dielectric properties of small tissue samples; Phys. Med. Biol.; 37(1); pp. 183-192; Jan. 1992.

Lehmann et al.; Therapeutic Heat; Therapeutic Heat and Cold, Fourth Ed.; Chapter 9; pp. 417-581; Williams & Wilkins (publishers), Baltimore, MD; Apr. 1990.

(56) References Cited

OTHER PUBLICATIONS

Lumenis Inc.; Aluma RF Skin Renewal System (product information); copyright 2007 (PB-1013670); 8 pgs.; Oct. 2007 (printed version).

Michel et al.; Design and Modeling of Microstrip—Microslot Applicators with Several Patches and Apertures for Microwave Hyperthermia; Microwave and Optical Technology Letters; vol. 14, No. 2; pp. 121-125; Feb. 5, 1997.

Shimm, D et al.; Hyperthermia in the Treatment of Malignancies; Therapeutic Heat and Cold Fourth Edition edited by Justin Lehmann M.D., Chapter 14, pp. 674-699, Williams & Wilkins Publishers, Baltimore, MD; Apr. 1990.

SRLI Technologies; BTC-2000} (product information); printed from website: http://www.srli.com/technologies/BTC2000.html on Nov. 16, 2009; 1 pg.

Stauffer et al.; Practical induction heating coil designs for clinical hyperthermia with ferromagnetic implants; IEEE Trans. on Biomedical Engineering; 41(1); pp. 17-28; Jan. 1994.

Stoy et al.; Dielectric properties of mammalian tissues from 0.1 to 100 MHz: a summary of recent data; Phys. Med. Bil.; 27(4); pp. 501-513; Apr. 1982.

Stuchly et al.; Diathermy applicators with circular aperture and corrugated flange; IEEE Trans on Microwave Theory and Techniques; MTT-28(3); pp. 267-271; Mar. 1980.

Stuchly et al.; Dielectric properties of animal tissues in vivo at frequencies 10 MHz—1 GHz; Bioelectromagnetics; 2(2); pp. 93-103; Apr. 1981.

Stuchly et al.; Dielectric properties of animal tissues in vivo at radio and microwave frequencies: comparison between species; Phys. Med. Biol.; 27(7); pp. 927-936; Jul. 1982.

Sullivan et al.; Comparison of measured and simulated data in an annular phased array using an inhomogeneous phantom; IEEE Trans on Microwave Theory and Techniques; 40(3); pp. 600-604; Mar. 1992.

Tavernier et al.; Conductivity and dielectric permittivity of dermis and epidermis in nutrient liquid saturation; Engineering in Medicine and Biology Society; 1992 14th Annual Int. Conf of the IEEE; Paris, France; pp. 274-275; Oct. 29-Nov. 1, 1992.

Thermolase Corp.; 510K Pre-Market Notification (No. K950019) and Product User Manual ThermoLase Model LT100 Q-Switched Nd: YAG, Laser Hair Removal System, Jan. 3, 1995.

Trembly et al.; Combined Microwave Heating and Surface Cooling of the Cornea; IEEE Transactions on Biomedical Engineering; vol. 38; No. 1; pp. 85-91; Jan. 1991.

UROLGIX, Inc.; Cooled Thermotherapy + Prostiva RF = Durability + Versatility; 1 pg.; printed Jun. 18, 2012 from website (http://www.urologix.com/).

Uzunoglu et al.; A 432-MHz Local Hyperthermia System Using an Indirectly Cooled, Water-Loaded Waveguide Applicator; IEEE Trans. on Microwave Theory and Techniques; vol. 35, No. 2; pp. 106-111; Feb. 1987.

VALLEYLAB; Cool-tip} RF Ablation System; (http://www.cool-tiprf.com/physics.html) accessed Jun. 24, 2008.

Vardaxis et al.; Confocal laser scanning microscopy of porcine skin: Implications for human wound healing studies; J Anat; 190(04); pp. 601-611; May 1997.

Vrba, et al.; Evanescent-Mode Applicators (EMA) for Superficial and Subcutaneous Hyperthermia; IEEE Trans. on Biomedical Engineering; vol. 40; No. 5; pp. 397-407; May 1993.

Wikipedia; ISM band; 5 pages; printed Jul. 22, 2014 from website (http://en.wikipedia.org/wiki/ISM_band).

Wonnell et al.; Evaluation of microwave and radio frequency catheter ablation in a myocardium-equivalent phantom model; IEEE Trans. on Biomedical engineering; 39(10); pp. 1086-1095; Oct. 1992.

Zhou et al.; Resection of Meningiomas with Implantable Microwave Coagualation; Bioelectromagnetics; vol. 17; No. 2; pp. 85-88; (year of publication is sufficiently earlier than the effective U.S. filing date and any foreign priority date) 1996.

Wikipedia; Bayonet mount; 6 pages; Dec. 18, 2014; retrieved from the internet (www.http://en.wikipedia.org/wiki/Bayonet mount).

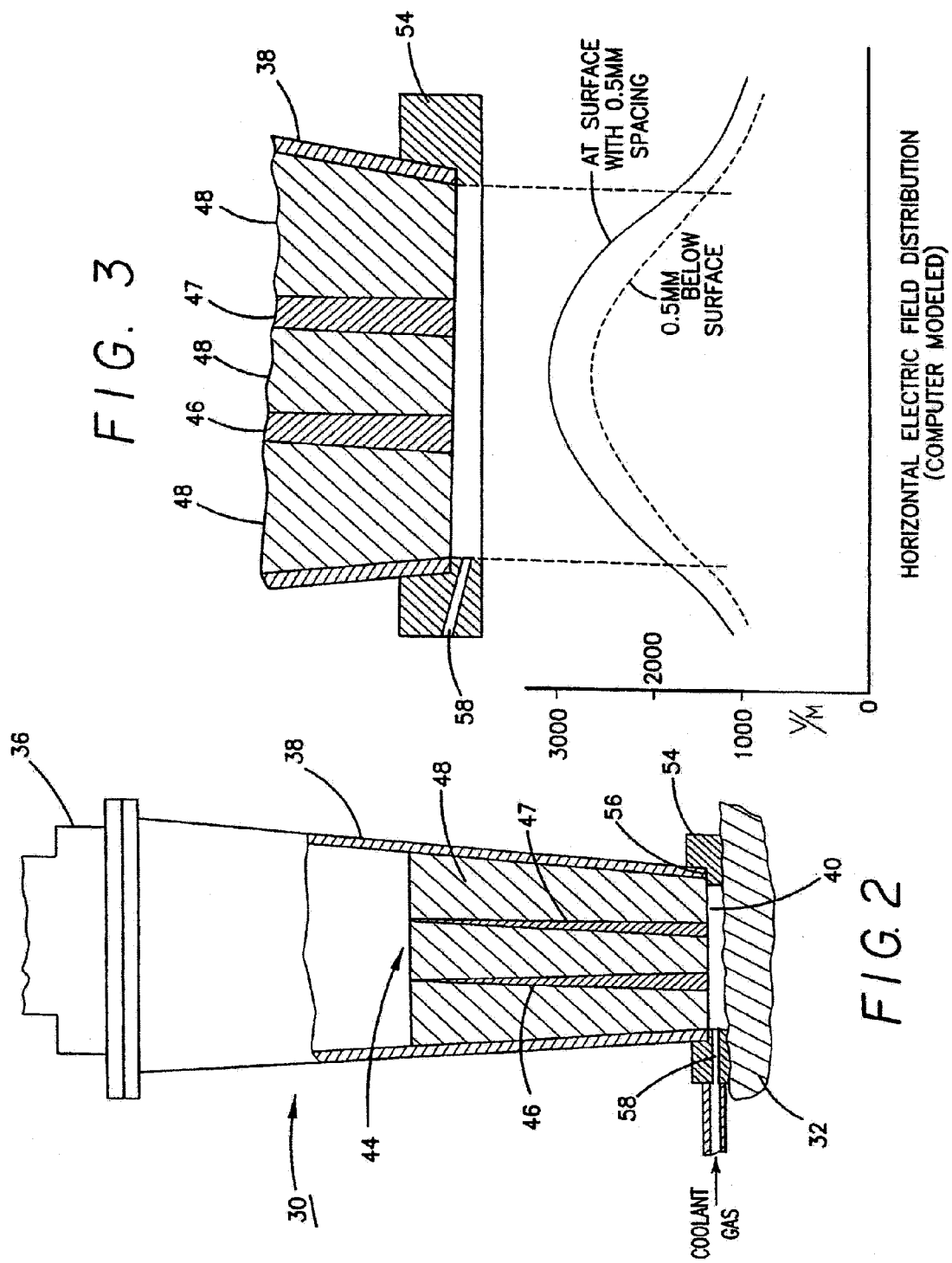

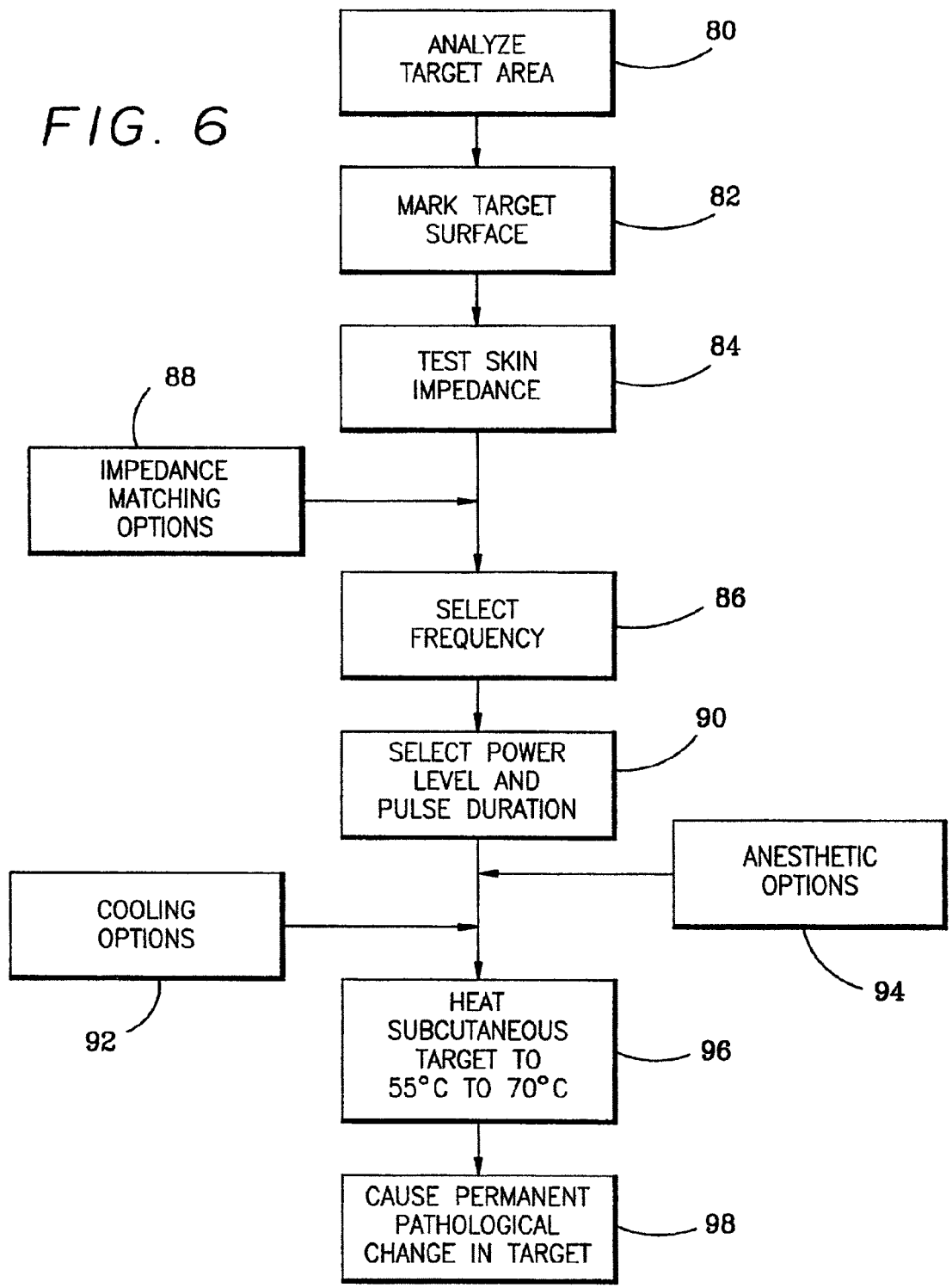

METHOD AND APPARATUS FOR TREATING SUBCUTANEOUS HISTOLOGICAL FEATURES

CROSS REFERENCE TO RELATED APPLICATIONS

This application is a continuation of U.S. application Ser. No. 13/673,144, filed Nov. 9, 2012, now U.S. Pat. No. 8,853,600, which is a continuation of U.S. application Ser. No. 13/280,032, filed Oct. 24, 2011, now U.S. Pat. No. 8,367,959; which is a continuation of U.S. application Ser. No. 09/637,923, filed Aug. 14, 2000, now U.S. Pat. No. 8,073,550; which is a divisional of U.S. application Ser. No. 08/904,175, filed Jul. 31, 1997, now U.S. Pat. No. 6,104,959; all of which are incorporated herein by reference.

FIELD OF THE INVENTION

This invention relates to effecting pathological changes in subcutaneous histological features so as to eliminate unsightly or potentially harmful vascular and cellular conditions, without side effects and with fewer steps and less discomfort than has heretofore been possible.

BACKGROUND OF THE INVENTION

Radiation therapy is an accepted treatment for a wide variety of medical conditions. High intensity radiant energy sources in the visible band, such as lasers, are now being widely used for both internal and extracorporeal procedures. While the microwave band, between 300 MHz and 30 GHz affords the capability of penetrating deeper than visible light while interacting differently with body tissue it has heretofore been employed primarily only in a variety of dissimilar medical procedures.

Microwave energy exerts its effect on tissue through controlled regional heating (hyperthermia) of affected features through interaction between the wave energy and magnetically polarizable tissue matter. By using microwaves to establish a regional hyperthermia, it is possible to preferentially increase the temperature of diseased or unwanted histological features to levels which are pathologically effective. At the same time, a necessary objective is to maintain adjacent tissue at acceptable temperatures, i.e., below the temperature at which irreversible tissue destruction occurs. Such microwave induced hyperthermia is well known in the field of radiology where it is used in the treatment of individuals with cancerous tumors.

A number of specific methods for treating histological features by the application of microwave radiation are described in the medical literature. For example, a technique for treating brain tumors by microwave energy is disclosed in an article entitled "Resection of Meningiomas with Implantable Microwave Coagulation" in Bioelectromagnetics, 17 (1996), 85-88. In this technique, a hole is drilled into the skull and a catheter is invasively inserted into the hole to support a coaxial radiator or antenna. Microwave energy is then applied to the antenna to cause the brain tumor to be heated to the point where the center of the tumor shows coagulative necrosis, an effect which allows the meningioma to be removed with minimal blood loss. Another technique in which microwave energy is utilized to treat prostate conditions is disclosed by Hascoet et al. in U.S. Pat. No. 5,234,004. In this technique, a microwave antenna in a urethral probe connected to an external microwave generating device generates microwaves at a frequency and power effective to heat the tissues to a predetermined temperature for a period of time sufficient to induce localized necrosis. In a related technique disclosed by Langberg in U.S. Pat. No. 4,945,912, microwave energy is used to effect cardiac ablation as a means of treating ventricular tachycardia. Here, a radiofrequency heating applicator located at the distal end of a coaxial line catheter hyperthermically ablates the cardiac tissue responsible for ventricular tachycardia. As with the described methods of tumor treatment, this method of cardiac ablation operates by preferentially heating and destroying a specifically targeted area of tissue while leaving surrounding tissue intact.

While the general principle of propagating microwave energy into tissue for some therapeutic effect is thus known, such applications are usually based on omnidirectional broadcasting of energy with substantial power levels. The potential of microwave energy for use with subcutaneous venous conditions and skin disorders has not been addressed in similar detail, probably because of a number of conflicting requirements as to efficacy, safety, ease of administration and side effects.

As a significant number of individuals suffer from some type of subcutaneous but visible abnormality, therapeutic techniques which effectively address these conditions can be of great value. Such features which are potentially treatable by microwave energy include conditions such as excessive hair growth, telangiectasia (spider veins) and pigmented lesions such as cafe-au-lait spots and port wine stains (capillary hemangiomas). Of these conditions, excessive hair growth and spider veins are by far the most common, affecting a large percentage of the adult population.

Unwanted hair growth may be caused by a number of factors including a genetic predisposition in the individual, endocrinologic diseases such as hypertrichosis and androgen-influenced hirsuitism as well as certain types of malignancies. Individuals suffering from facial hirsuitism can be burdened to an extent that interferes with both social and professional activities and causes a great amount of distress. Consequently, methods and devices for treating unwanted hair and other subcutaneous histological features in a manner that effects a permanent pathological change are very desirable.

Traditional treatments for excessive hair growth such as depilatory solutions, waxing and electrolysis suffer from a number of drawbacks. Depilatory solutions are impermanent, requiring repeated applications that may not be appropriate for sensitive skin. Although wax epilation is a generally safe technique, it too is impermanent and requires repetitive, often painful repeat treatments. In addition, wax epilation has been reported to result in severe folliculitis, followed by permanent keloid scars. While electrolysis satisfactorily removes hair from individuals with static hair growth, this method of targeting individual hairs is both painful and time consuming. In addition, proper electrolysis techniques are demanding, requiring both accurate needle insertion and appropriate intensities and duration. As with wax epilation, if electrolysis techniques are not performed properly, folliculitis and scarring may result.

Recently developed depilatory techniques, utilizing high intensity broad band lights, lasers or photochemical expedients, also suffer from a number of shortcomings. In most of these procedures, the skin is illuminated with light at sufficient intensity and duration to kill the follicles or the skin tissue feeding the hair. The impinging light targets the skin as well as the hair follicles, and can burn the skin, causing discomfort and the potential for scarring. Further, laser and other treatments are not necessarily permanent and may require repeated applications to effect a lasting depilation.

Like hair follicles, spider veins are subcutaneous features. They exist as small capillary flow paths, largely lateral to the skin surface, which have been somewhat engorged by excessive pressure, producing the characteristic venous patterns visible at the skin surface. Apart from the unsightly cosmetic aspect, telangiectasia can further have more serious medical implications. Therefore, methods and devices for treating spider veins and other subcutaneous histological features in a manner that effects a permanent pathological change to the appropriate tissues are highly desirable.

The classical treatment for spider veins is sclerotherapy, wherein an injection needle is used to infuse at least a part of the vessel with a sclerotic solution that causes blood coagulation, and blockage of the blood path. With time, the spider veins disappear as the blood flow finds other capillary paths. Since there can be a multitude of spider veins to be treated over a substantial area, this procedure is time-consuming, tedious, and often painful. It also is of uncertain effectiveness in any given application and requires a substantial delay before results can be observed.

Another procedure for the treatment of shallow visible veins, which is similar to techniques used in depilation, involves the application of intense light energy for a brief interval. This technique exposes the skin surface and underlying tissue to concentrated wave energy, heating the vein structure to a level at which thermocoagulation occurs. In particular, these energy levels are so high that they cause discomfort to some patients, and they can also be dangerous to those in the vicinity, unless special precautions are taken. In addition, some patients can be singed or burned, even though the exposure lasts only a fraction of a second.

Due to the serious problems that the subcutaneous abnormalities can create in individuals, there is a general need to be able to treat such features in a manner that effects beneficial pathological change without adverse side effects or discomfort. An optimal therapeutic technique should effect a permanent pathological change without requiring repeated applications to reach the desired effect. Moreover, these procedures should be noninvasive, should cover a substantial target area that is not limited to a single hair follicle or spider vein, and should make optimum use of the energy available. Finally, pathological changes should occur only in the targeted feature, and not in intervening or underlying layers.

SUMMARY OF THE INVENTION

The present invention overcomes the deficiencies in previously described methods for treating subcutaneous features by delivering a dosage of microwave energy that is maintained for only a short duration but at an energy level and at a wavelength chosen to penetrate to the depth of a chosen histological feature. The subcutaneous features are destroyed or pathologically altered in a permanent fashion by the hyperthermic effect of the wave energy while the surrounding tissue is left intact.

In accordance with the invention, the effective delivery of microwave energy into the subcutaneous feature can be maximized in terms of both the percentage of energy transmitted into the body and a preferential interaction with the target feature itself. The microwave energy is specifically targeted to the chosen depth and the targeted feature is heated internally to in excess of about 55° C., to a level which thromboses blood vessels and destroys hair follicles. The ability to target a wide area containing a number of features simultaneously enables a single procedure to supplant or reduce the need for repetitive applications.

Methods in accordance with the invention utilize certain realizations and discoveries that have not heretofore been appreciated in relation to wave energy-tissue interactions at a substantial depth (up to 5 mm below the skin surface). The wavelengths that are selected are preferentially absorbed by a targeted feature such as a blood vessel more readily than by skin surface and tissue. Thus, a chosen frequency, such as 14 GHz, penetrates through surface tissue to the chosen depth of the target feature, but not significantly beyond, and the energy heats the target more than adjacent tissue. Dynamic thermal characteristics are also taken into account, because transfer of thermal energy from small target features such as minute heated blood vessels to the surrounding tissue (the "thermal relaxation time") is much faster than that for larger vessels. The duration of a dosage, typically in the range of 100 milliseconds, is varied to adjust for this size factor.

Immediately prior to, concurrently with, or after the application of penetrating microwave energy, the skin surface is advantageously cooled. This cooling may be effected in a number of ways such as through the delivery, as rapidly expanding gas, of known coolants into a small space between the microwave emitter and the skin surface. The use of coolant enables the surgeon not only to minimize patient discomfort and irritation, but also to adjust energy dosages in terms of intensity and duration, because heat extraction at the surface also affects heating to some depth below the surface. The surgeon can also employ air cooling to minimize irritation while assuring results over a larger subcutaneous area and with fewer applications.

While it is advantageous to cool the skin surface with a separate medium in the target area immediately prior to or during wave energy application, it is also shown that the wave energy emitting device itself can be used to draw thermal energy off the skin surface. Again, the skin is heated minimally, giving the patient little, if any discomfort, and avoiding skin irritation. Comfort may be ensured for sensitive patients by a topical anesthetic, or by a conductive gel or other wave energy complementary substance introduced between the applicator and the skin surface.

The energy applied is generally in excess of about 10 Joules, and the duration is typically in the range of 10 to 1,000 milliseconds, with about 100 milliseconds being most used. The total energy delivered is typically in the range of 10-30 Joules, although the energy delivered as well as frequency may be changed in accordance with the nature of the targeted features, the target volume and depth. In a depilation process, for example, 10 to 20 Joules will usually suffice when a compact applicator is used, while a higher input level, such as 20 to 30 Joules, is used for a telangiectasia treatment.

A system in accordance with the invention for use in such procedures may employ a tunable power generator, such as a tunable power source operable in the microwave range from 2.45 GHz to 18 GHz, and means for gating or otherwise controlling the power output to provide selected pulse durations and energy outputs. The system also can incorporate power measurement sensors for both forward power and reflected power or circuits for measuring impedance directly. Thereby, tuning adjustments can be made to minimize reflection. Power is delivered through a manipulatable line, such as a flexible waveguide or coaxial line, to a small and conveniently positionable applicator head which serves as the microwave launcher or emitter. The applicator head may advantageously include, in the wave launching section, a dielectric insert configured to reduce the applicator cross-section, and to provide a better match to the impedance of the skin surface. Furthermore, the dielectric insert is chosen so as to distribute the microwave energy with more uniform intensity across the entire cross section, thus eliminating hot spots and covering a larger area.

If the dielectric is of a material, such as boron nitride or beryllium, oxide, which is a good thermal conductor, it can be placed in contact with the skin and thermal energy can be conducted away from the skin as microwave energy is transferred. Different clinical needs can be met by making available a number of different dielectric element geometries fitting within an interchangeable mount. The applicator head may further include a pressure limiting mechanism to insure that the head does not compress vessels as the procedure is being carried out.

In addition to the range of capabilities thus afforded, the surgeon can use ultrasound or other inspection techniques to identify the locations of the subcutaneous features for the precise mapping of target sites. Using an indexing or aiming device or element on the applicator head, energy can be applied a minimum number of times at precise locations to encompass a maximum number of targets. Because skin and tissue characteristics vary, pretesting target characteristics and varying the frequency or phase applied can increase efficiency and reduce the possibility of side effects.

In another application in accordance with the invention, the skin target area may be more readily visualized by using a microwave launcher positionable within an end unit in one of two alternate positions. In one position, the target area can be viewed and the launcher indexed for movement into precise proximity to the target area. In yet another example, a rectangular waveguide of standard size and therefore larger cross-section is used, with air cooling of the skin surface. For depilation, a peel-off, attachable label locating a number of delineated contiguous target areas can be placed on the skin. When the applicator has been energized at each target area, the label sheet can be peeled off, removing hair residue with it.

The applications of the process and method are not limited to conditions such as spider veins and unwanted hair, but further encompass pigmented lesions and related abnormalities, as well as other temporary and permanent skin disorders.

BRIEF DESCRIPTION OF THE DRAWINGS

A better understanding of the invention may be had by reference to the following specification, taken in conjunction with the accompanying drawings, in which:

FIG. 2 is a side view, partially in section, of a microwave applicator for use in the system of FIG. 1;

FIG. 3 is a fragmentary view of the beam launching end of a microwave applicator in relation to a graphical representation of electric field strength across the applicator;

FIG. 6 is a simplified depiction of method steps in accordance with the invention;

DETAILED DESCRIPTION OF THE INVENTION

Figure 1:
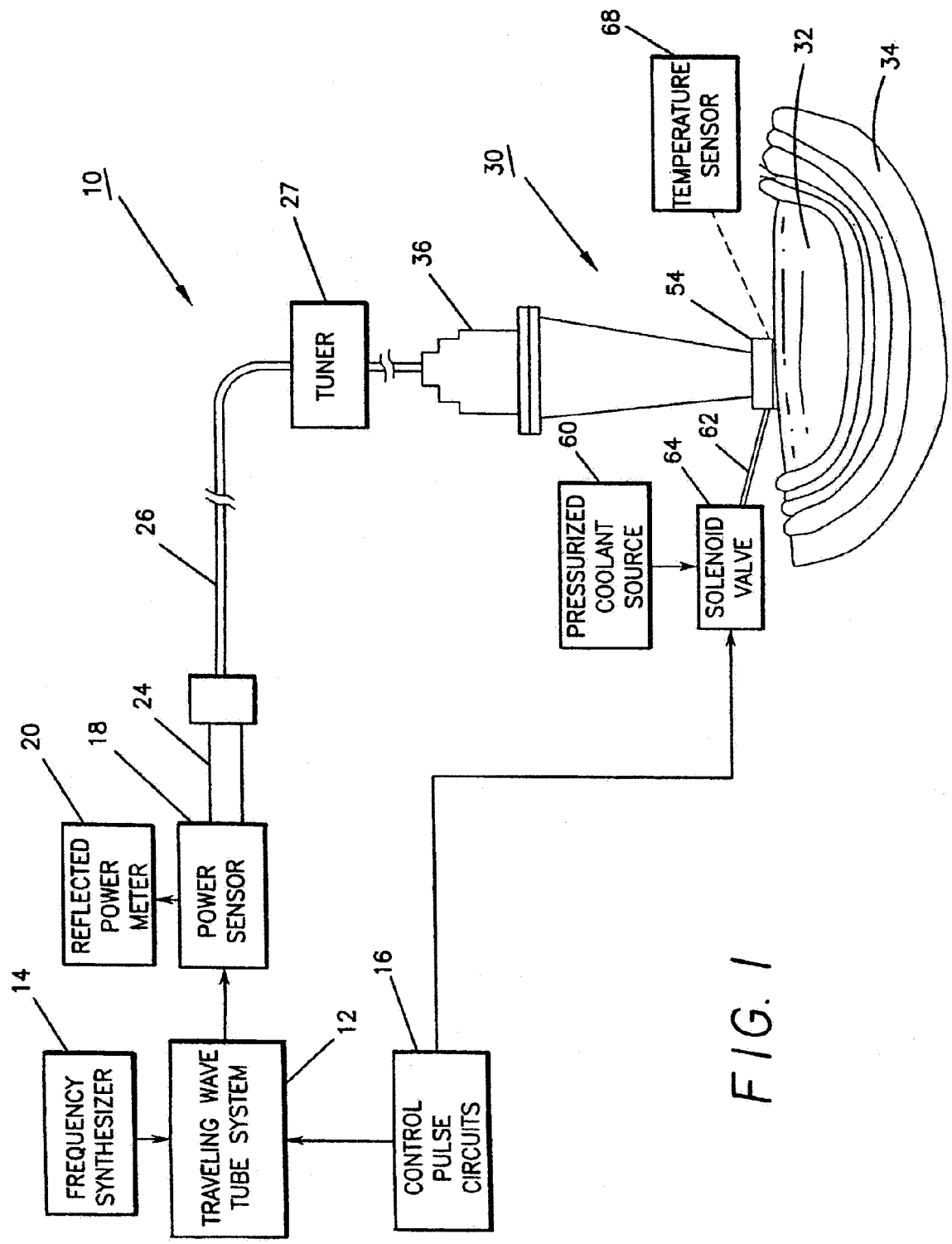
FIG. 1 is a combined block diagram and perspective view of a system in accordance with the invention.

A system in accordance with the invention; referring now to FIG. 1, is depicted in an example intended for use in hair removal, the treatment of spider veins and other skin disorders. This configuration includes a hand-held applicator that is suitable for potential use at any frequency within a suitable range, as well as for measurement of skin or tissue properties. Such a system can be used for treating any of a variety of skin disorders, including hirsuitism, telangiectasia, pigmented lesions and the like. It will be apparent to those skilled in the art that where such degrees of versatility and usage in different possible applications are not required, a simpler and less expensive system will often suffice. In addition, if a manually movable applicator head is not required, the system can be simplified in this respect as well. In the most rudimentary example, a monofrequency unit with means for adjusting dosage driving a fixed applicator head may be adequate.

Referring to FIG. 1, in a system 10 in accordance with the invention microwave energy of a selected frequency can be generated by any one of a number of conventional devices, such as a variable frequency synthesizer 14 that covers a range from about 2 GHz to about 20 GHz. A number of other conventional microwave generators are tunable in the range of 2.45 GHz to 18 GHz, for example, but here a suitable combination includes the frequency synthesizer 14 and a traveling wave tube system 12 having internal power and a high power output amplifier. Where operating conditions are well-defined and wide tunability is not needed, a conventional low cost source such as a magnetron may be used. The output of the traveling wave tube system 12 is gated open for selected intervals by control pulse circuits 16, which can be set, in this example, for any interval from 10 to 1000 milliseconds. Thus, the selected frequency is delivered as a pulse burst to provide from 50 W to as much as 4 KW output, the power level most often being of the order of a few hundred watts. In transmission to the operative site, the power bursts are directed through a power sensor 18, which diverts both forward and reverse propagated energy samples to a power meter 20. Readings at the power meter 20 enable the surgeon to fine tune power, phase or frequency settings to improve impedance matching and energy efficiency.

Preinspection of the target site is dependent on the nature of the target. Although visual inspection is sometimes alone sufficient for target area selection, as with hirsuitism, target veins at depth below the surface can often better be identified, located, and dimensioned by conventional analytical instruments, such as those using ultrasound imaging. As is described hereafter, the power, duration and frequency applied can also be adjusted in relation to the thermal relaxation characteristics of a target blood vessel, which in turn is dependent on size and location.

A microwave transmission line 24, here including a flexible rectangular waveguide or a flexible coaxial section 26 that may be manually manipulated, supplies the microwave energy through a phase shifter or other kind of tuner 27 to a hand applicator 30 shown here as positioned against a limb 32 exposed within a surgical drape 34. The handpiece 30, shown in greater detail in FIGS. 2 and 3, is essentially a rectangular waveguide device having a stepped or other impedance matching section 36 coupled to the flexible coaxial line 26. The handpiece 30 includes a converging tapered body 38 having an open aperture end 40 serving as the wave launching terminus. Internal to the tapered waveguide section 38 is a dielectric insert 44 here formed of two high dielectric (K=16) tapered strips 46, 47 held in place between low dielectric constant (K=2.5) spacers 48 of a virtually microwave transparent material such as "Rexolite". This configuration of dielectrics, as seen in FIG. 3, spreads the electric field distribution toward the sidewalls, enlarging the target area that is effectively acted upon by the wave energy and eliminating any hot spot tendency within the target area. In addition, the dielectric insert 44 provides a better impedance match to the skin, reducing reflective losses, which can further be minimized by adjustments at the tuner 27. The dielectric 44 also reduces the cross-sectional area and size of the waveguide, thereby making the handpiece 30 easier to handle. In addition, the internal taper matches the waveguide impedance to the different impedance of the dielectric loaded section, so as to minimize reflection.

The flexible coaxial line 26 allows a surgeon to move the applicator 30 to place its open end manually wherever desired on the body surface 32. At the frequency range of 12-18 GHz, a standard WR 62 waveguide section with 0.622"×0.311" orthogonal dimensions can be employed at the output end of the impedance matching section 36. The tapered section 38, loaded by the dielectric 44 in this example, reduces the waveguide dimension to 0.250"×0.150" at the output terminal face 40. The end face 40, however, is set off from the limb or other body surface 32 against which it is juxtaposed by an encompassing and intervening spacer element 54, best seen in FIGS. 2 and 3. The spacer element 54 includes an interior shoulder 56 extending around the periphery of the end 40 of the tapered section 38, defining a standoff volume of a height of about 0.020" (0.5 mm). A coolant can thus be injected via a side conduit 58 from a pressurized coolant gas source 60 (FIG. 1), via a coupling conduit 62 extending through a solenoid controlled valve 64. The pulse control 16 opens the valve 64 in timed relation to the microwave pulse to be delivered from the traveling wave tube system 12. This timing relation can be controlled, so that the target skin area can be precooled prior to delivery of the microwave pulse, cooled concurrently with the delivery or cooled after the start of the delivery of the microwave pulse. Furthermore, a temperature sensor 68, shown only generally in FIG. 1, may be disposed within the standoff volume, in contact with the skin or otherwise, to sense the lowering of temperature at the target surface. In this example, the coolant is a pressured gas, such as 1,1,1,2 tetrafluoroethane, held under high pressure in liquefied or gaseous phase. When injected by actuation of the valve 64, the gas expands vigorously within the standoff volume, rapidly lowering the temperature because of the expansion effect. Since the boiling point of the tetrafluoroethane is approximately −26° C. at 1 atm, it is extremely effective in extracting thermal energy from the target area, even for the short bursts of the order of a fraction of a second that are involved in the present procedure. The temperature sensor 68 may be a Luxtron fiber optic device for measuring temperature, or it may be a thermistor which is coupled in a circuit that triggers the microwave pulse when the coolant has adequately lowered the temperature at the skin surface or in the standoff volume. Other coolants, including air, can alternatively be used to reduce the skin surface temperature within the standoff volume during the procedure.

Other alternative approaches may be utilized to minimize discomfort and, separately or additionally, provide improved efficiency. A compound that is complementary to the delivery of the microwave energy, in the sense of neither being reflective or absorptive, and therefore not appreciably heated, can be placed on the skin prior to microwave pulse application. For example, a topical anesthetic having short term effectivity may be all that is needed to reduce the discomfort of some patients to an acceptable level. Other patients may require no coolant or topical anesthetic whatsoever. Another alternative is to employ a surface gel or other substance that improves impedance matching between the microwave pulse launching device and the surface tissues.

The microwave delivery system provided by the applicator 30 delivers microwave energy over an advantageously broad field distribution into a subcutaneous surface area as best understood by reference to FIG. 3. The dielectric loading introduced by the spaced apart dielectric elements 46, 47, which diverge toward the output end as the sidewalls converge in the tapered section 38, alters the normal horizontal electric field distribution from its normal half sine wave characteristic so that there is substantial field strength at the two sidewalls and no high central energy peak. A single, appropriately shaped, dielectric element can be used to modify the field distribution to like effect. By thus spreading the energy across the target area, there is both elimination of localized energy concentrations (and therefore localized heating) and a larger effective treatment area. As seen in the graphical portion of FIG. 3, in the solid line, the calculated electric field at the skin surface when the outlet end 40 of the microwave launcher is 0.5 mm off the surface, is more than twice that at the edges. This differential is reduced when the field distribution is modeled at a depth of 0.5 mm below the skin surface. In both instances, there is a degree of dispersion outside the perimeter of the applicator face 40 because of the setoff spacing, but this aids in equalizing the power distribution and poses no radiation danger.

Figure 7:
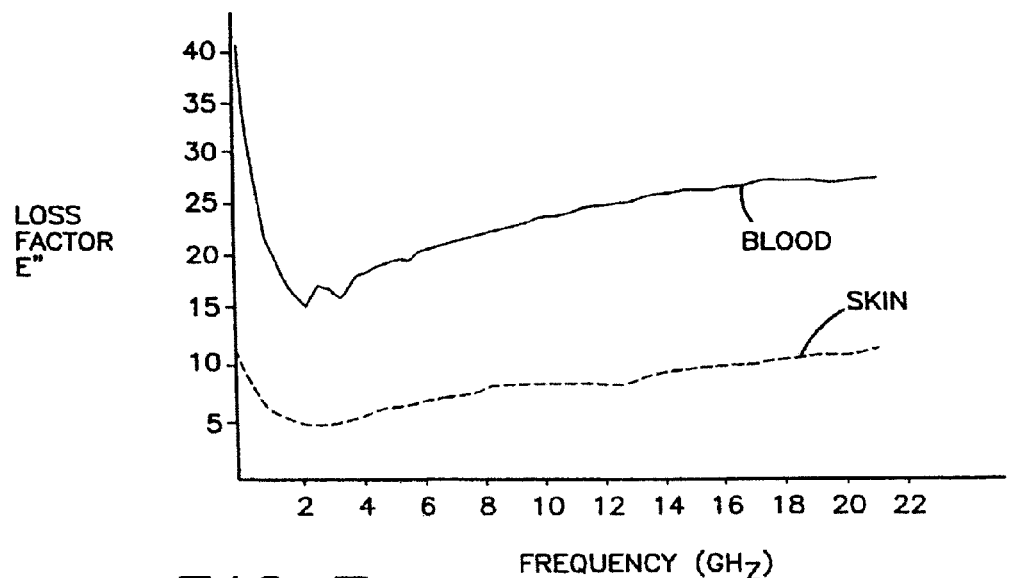
FIG. 7 is a graphical depiction of loss factor curves showing the comparative absorption of microwaves in blood and tissue at different frequencies.

In accordance with the present invention, advantage is taken of the results of an analysis of the interaction of microwaves with biological tissues at different frequencies. The complex permittivity $\in^*$ of any given matter, including biological matter, in a steady state field is conventionally analyzed using the following equation:

$$\in^* = \in_0 (\in' - j\in''),$$

in which $\in_0$ is the dielectric constant of free space and the real component, $\in'$, is the dielectric constant, while the imaginary component, $\in''$ is the loss factor. As seen in FIG. 7, the loss factor ($\in''$) of blood, in the range of 2 to 20 GHz, shown by tests to be substantially higher than that of skin tissue. Further analysis has ascertained that by considering both relative and absolute factors, the most advantageous conditions exist at about 14 GHz. From published work, the dielectric constant of skin is known to be about 22 at 10 GHz and to decrease with increasing frequency to a value of 12 at 18 GHz. The loss factor for skin reaches a peak of 18 at 9 GHz and decreases with increasing frequency to a value of 12 at 14 GHz. The loss factor $\in''$ for skin is approximately one-half that for blood in the frequency range between 14 GHz and 20 GHz, and above 10 GHz the loss factor for blood increases somewhat more than for skin, as seen in FIG. 7. Therefore, the heat generated per unit volume in blood and to some extent in differentiable cellular structures other than skin, can be expected to be twice that of skin. Consequently, differential heating results when microwave energy penetrates subcutaneous regions. Because these subcutaneous regions are of depths up to 5 mm, they are directly within the range of interest that includes hair follicles and roots, telangiectasia, pigmented lesions, and other histological features that are visible through the epidermis and/or dermis, or actually protrude at the skin.

Figure 4:
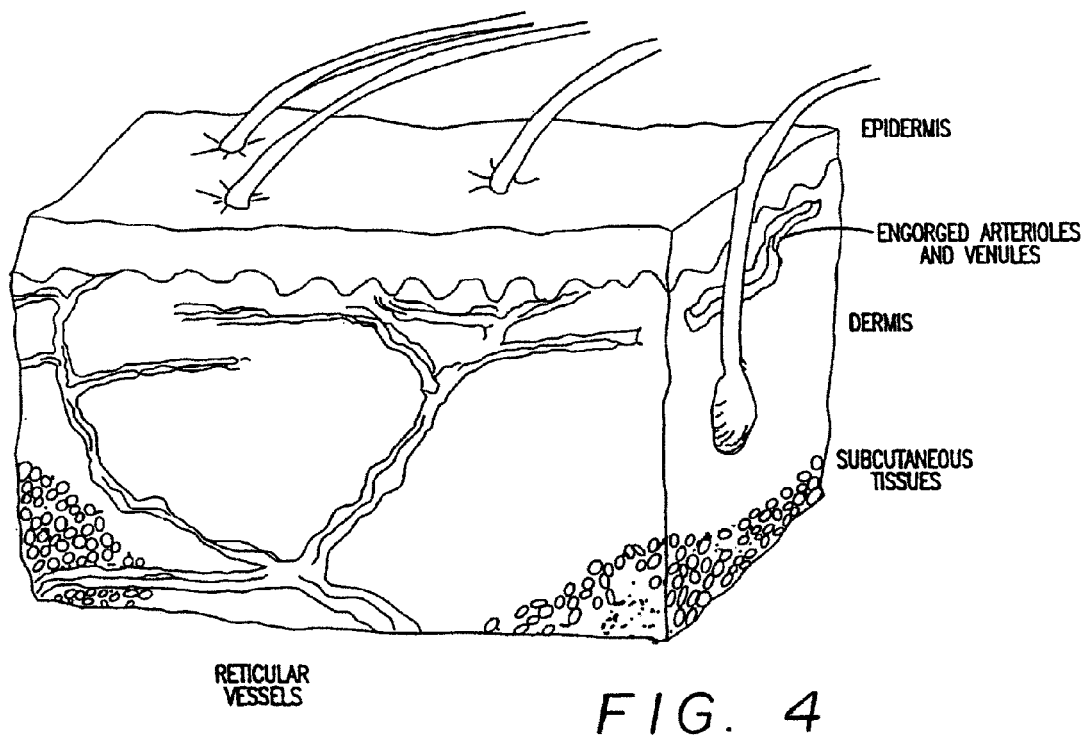
FIG. 4 is a simplified, perspective view of a section of subcutaneous structure, depicting different layers therein in relation to blood vessels and hair follicles.

The structure of skin is somewhat idealistically and simplistically depicted in FIG. 4, in order to show the physical relation and relative proportions (although not to scale) between the epidermis and dermis layers that lie above subcutaneous tissue, and to further represent histological features of interest in the structure. Sweat glands, nerve endings, corpuscular structures and sebaceous glands are not included for clarity. The hair shafts, most deeply embedded at their roots at 4 to 5 mm depth in the dermis, extend outwardly through the dermis and the relatively more robust epidermal layer. Relatively large arteries and veins branch into the arteriole and venule vessels which feed and derive blood, respectively, as the smallest capillaries that normally are invisible from the skin surface, and that form the termini of the blood paths. When these capillaries, either or both arterioles and venules, become engorged for some reason, as in the telangiectasia condition, they form the lateral and visible pattern, known collectively as spider veins, at a depth of 0.1 to 1.0 mm below the surface of the epidermis. Typically of the order of 0.2 mm in diameter, the spider veins can actually sometimes protrude at the surface, and be larger in diameter as well. Reticular or feeder veins can lie as much as 5 mm in depth below the surface, and are substantially larger, of the order of 1.0 to 2.0 mm in diameter, being large enough to be identified by a non-invasive inspection technique, such as imaging with ultrasound. The reticular or feeder veins sometimes create the overpressure condition causing engorgement of the spider veins.

Figure 5:
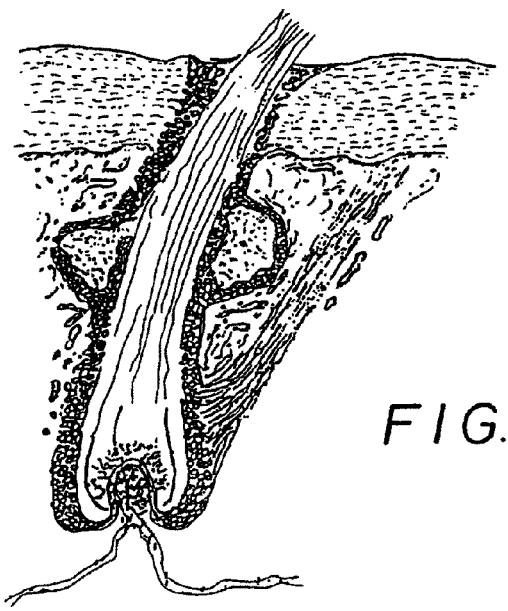
FIG. 5 is an enlarged sectional view of a hair structure from root to shaft.

FIG. 5 shows further details, again somewhat idealized, of an enlarged hair shaft, extending outwardly from a root into the growing cellular structure of the follicle and the follicle casing that transforms into the hair shaft body that passes through the epidermis. The hair follicle is nourished by at least one artery that feeds the papillae structure at the root and is encompassed in a crown of associated matrix cells. Attack on the cellular follicle structure or on the papillae or the arterioles or venules to and from the papillae can result in permanent destruction of the hair shaft.

With these considerations in mind, appreciation of the operation of the system of FIG. 1 can more readily be gained. The surgeon can use a suitable frequency for a chosen histological feature within the range of the frequency synthesizer 14. It is assumed here that the frequency chosen is about 14 GHz. The traveling wave tube system 12 is set to generate approximately 100 to 300 watts, the control pulse circuits 16 being set to open the solenoid valve 64 prior to getting a short pulse from the microwave system 12. It has been found that a 100 millisecond pulse is satisfactory for both efficacy and safety, although other durations can be used with wattage adjustments to compensate. The output from the traveling wave tube system 12 is directed through the power sensor 18, the transmission line 24, the flexible section 26, through the tuner 27 and to the applicator 30. If the operator desires, short test pulses of low amplitude can first be sent to obtain readings of the reflected power at the power meter 20, and fine tuning adjustments can be made at the tuner 27, in a conventional manner. In addition, the operator can use ultrasound or another non-invasive diagnostic system to analyze the substructure to identify the position of target features, such as reticular veins and arteries, both as to size and location. The procedure initially to be described, however, pertains to depilation, so that the target area is not only readily visible, but is also substantially uniform in depth and structure, as per FIG. 5.

When the control pulse circuits 16 operate, they first provide a control impulse to open the solenoid valve 64, in this example, and then turn on the traveling wave tube system 12 for the selected interval. Because the valve requires a few milliseconds (e.g., 20 to 35) to operate and a few milliseconds are also needed for the pressurized coolant from the source 60 to pass through the outer conduit 62 and the side conduit 58 in the spacer 54, it is preferred to delay the microwave pulse until cooling has actually begun or is contemporaneously begun. Alternatively, as previously noted, a temperature sensor 68 that detects a temperature drop at the skin surface may be used to either trigger the microwave pulse or to preclude its operation until after the coolant has become effective.

For depilation, pulses in the range of 10 to 20 Joules in terms of total work output have been shown to effect permanent depilation without significant discomfort or significant adverse side effects. Tests were run using the dielectric loaded applicator 30 having a 0.250"×0.150" output area (5 mm×3 mm, or 15 mm$^2$), and employing a pulse duration of 100 milliseconds in all instances. A substantial number of experiments were run on test rabbits with this applicator, varying only the power applied so as to change the total energy in Joules. The results were examined by a pathologist and the accompanying Tables 1 and 2, appended following the specification, show the results of his examination.

The system of FIG. 1 was also employed in a number of tests on rabbits to determine the changes occurring in veins and arteries under different pathological changes, and side effects on tissues and vessels with a protocol using cooling as well as no cooling to determine if pigmentation has an effect are shown in appended Table 3. These tests showed no significant difference in pigmentation versus non-pigmentation; indicating that coloration, and/or the presence of melanin, is not a significant factor in absorption of microwave energy. A different protocol was followed in amassing results shown in appended Table 4, which represents an analysis by a pathologist blinded to the dosages used. Cooling was not used in this example. These results with test rabbits show that pigmentation is not a significant factor and that at 16 Joules dosage and above, there is effective occlusion of target veins and arteries with minimal changes or only mild induration of tissues. The indication of dermal fibrosis again is not indicative of scar development.

Pathological examination of these animal studies consistently demonstrated destruction of hair follicles over a wide range of microwave energy levels. The destruction extended to the base of the follicle, which is significant to permanent hair removal. The amount of hair destruction within the target area varies in accordance with the total amount of energy, but destruction is substantially complete at 14 Joules and higher. Furthermore, until the energy delivered is in excess of 20 Joules, the appearance of the skin is normal in all cases and the epidermis is histologically intact. Minor indications of dermal fibrosis are not indicative of clinical scar formation. Minor vascular changes, such as intimal fibrosis of small arteries, constitute neither damaging nor permanent conditions. Consequently, a dosage in the range of 14 to 20 Joules is found both to be effective and to be free of deleterious side effects.

Figure 8:
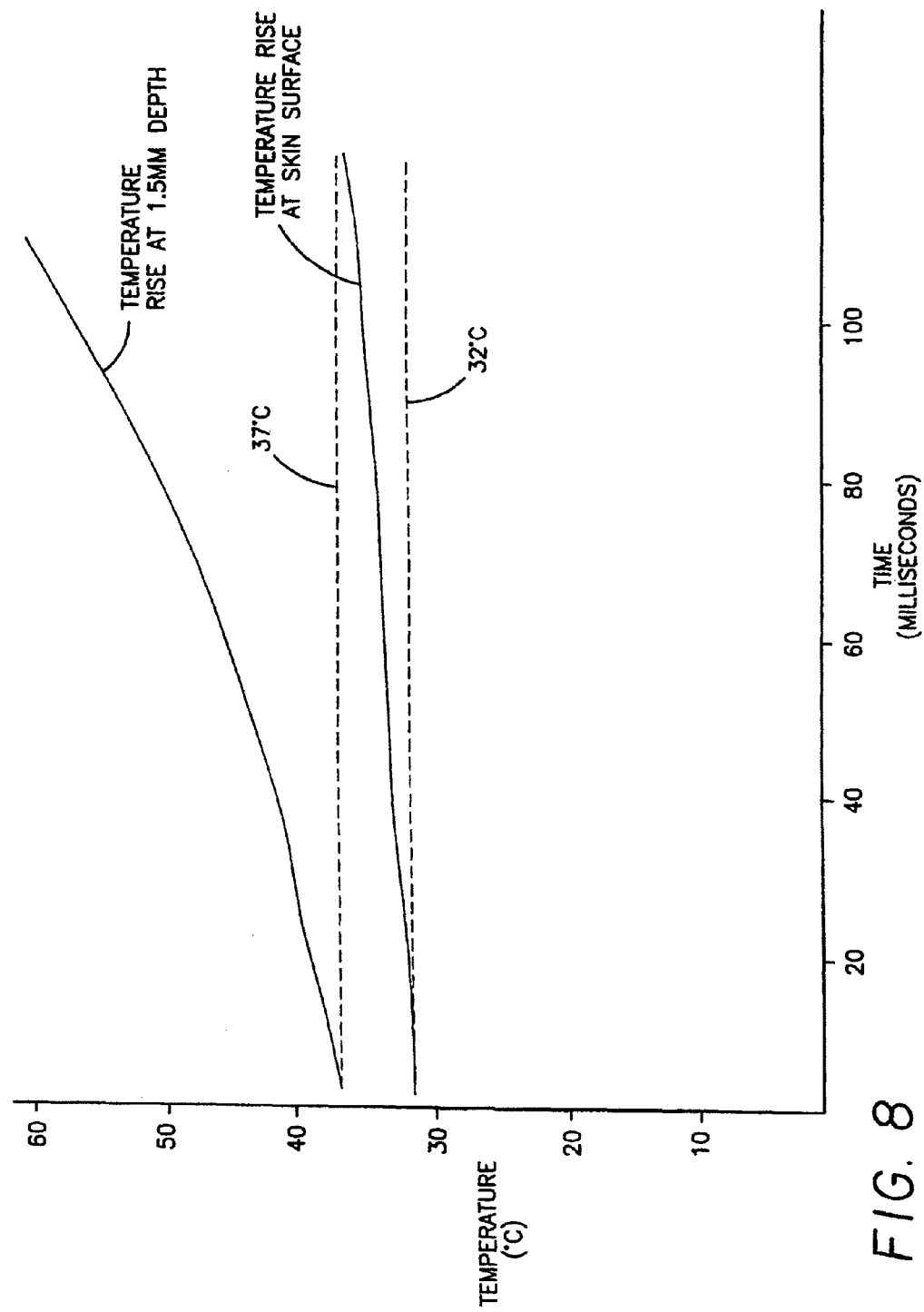
FIG. 8 is a graphical depiction of the temperature changes at and below the skin surface during practice of methods in accordance with the invention.

The effects of delivery of microwave energy, with surface cooling, are illustrated graphically in FIG. 8, which indicates temperature changes at both the surface of animal skin tissue (0.75 mm thick) and 1.5 mm below the surface, in water, under conditions of delivery of up to 12 Joules total energy level over 100 milliseconds duration, accompanied by cooling using expanded tetrafluorethane gas. As shown, the baseline temperature for the test animal skin is approximately 32°

C., and that for the body at a depth of 1.5 mm is approximately 37° C. Applying the microwave energy with cooling, the skin surface temperature rose very slightly, but was essentially unchanged. Beneath the skin surface, however, the temperature rise at 1.5 mm depth was at a substantially higher rate, reaching approximately 60° C. at 100 milliseconds. Higher temperatures would of course be reached with the application of higher energy levels. It is posited that even such a temperature is sufficient to cause cellular degradation of the hair follicles near the root, and it may well also thermocoagulate blood in the feeder artery, in the papillae at the hair root, or in the cell matrix surrounding the papillae. Although the hair follicles are not conductive, they may be particularly susceptible to the impinging microwave energy because they are thin dielectric elements which can cause energy concentration and therefore greater heating. Whether one or more effects are observable, permanent destruction has been shown by pathological examination, as in the annexed tables.

The microwave energy does not significantly penetrate beyond the depth of the targeted histological features because of attenuation, the limitation on total energy delivered and the lower loss factor in tissue.

Where the histological defects are benign vascular lesions, as with the telangiectasia condition, different tests and operating conditions may be employed, as shown in the steps of FIG. 6, to which reference is now made. While spider veins can cover a substantial area, and visual targeting may be sufficient, it is often desirable to analyze the target area in greater detail. Thus, ultrasound examination may be utilized to identify and estimate the size of reticular veins feeding a substantial area of spider veins, as an optional first step 80, which can precede marking of the target surface 82 in any appropriate way. Again, the dielectric constant, skin impedance or other characteristics may be tested in a preliminary step 84, prior to choosing operative frequency in step 86. Fine tuning, phase adjustment or another impedance matching option 88 may be employed to reduce reflective losses and increase efficiency. Given the size and location of the target vascular feature, thereafter, the power level and pulse duration may be selected in a step 90.

Figure 9:
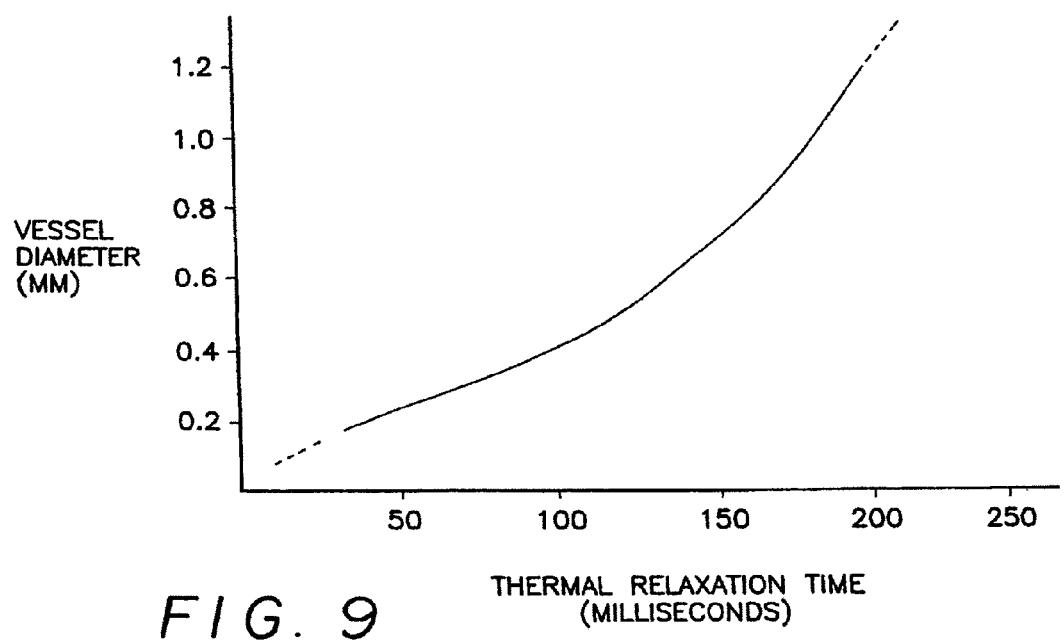
FIG. 9 is a graphical depiction of the variation in thermal relaxation time for different blood vessel diameters.

The pulse duration is a significant parameter in relation to the vessel diameter, since the smaller the vessel diameter, the shorter is the thermal relaxation time. Even though the loss factor of blood is higher than that of the tissue, dissipation of heat to surrounding tissue is much faster with a small blood vessel and consequently shorter term heating is needed. As seen in FIG. 9, thermal relaxation time increases monotonically with vessel diameter, and thus a longer duration pulse is needed, perhaps at the same or a greater power, if the vessel diameter is of a larger size. Given the power level and pulse duration, the operator can select one of the cooling options, which also includes no cooling whatsoever, in step 92. Typical anesthetics or other anesthetics may be employed at the same time, as shown by optional step 94.

Consequently, when the microwave pulse is delivered, the subcutaneous target is heated to the range of 55° C. to 70° C., sufficient to thrombose the vascular structure and terminate flow permanently. The specific nature contributing factors to disappearance of the vessels with time may be one or more factors, including thermocoagulation of the blood itself, heating of the blood to a level which causes thrombosis of the vessel or some other effect. The net result, however, is that a fibrous structure forms in the vessel which clogs and terminates flow, so that the resultant fibrous structure is reabsorbed with time, as new capillary flow paths are found. In any event, heating in the 55° C. to 70° C. is sufficient to effect (step 96) the permanent pathological change that is desired (step 98).

Figure 10:
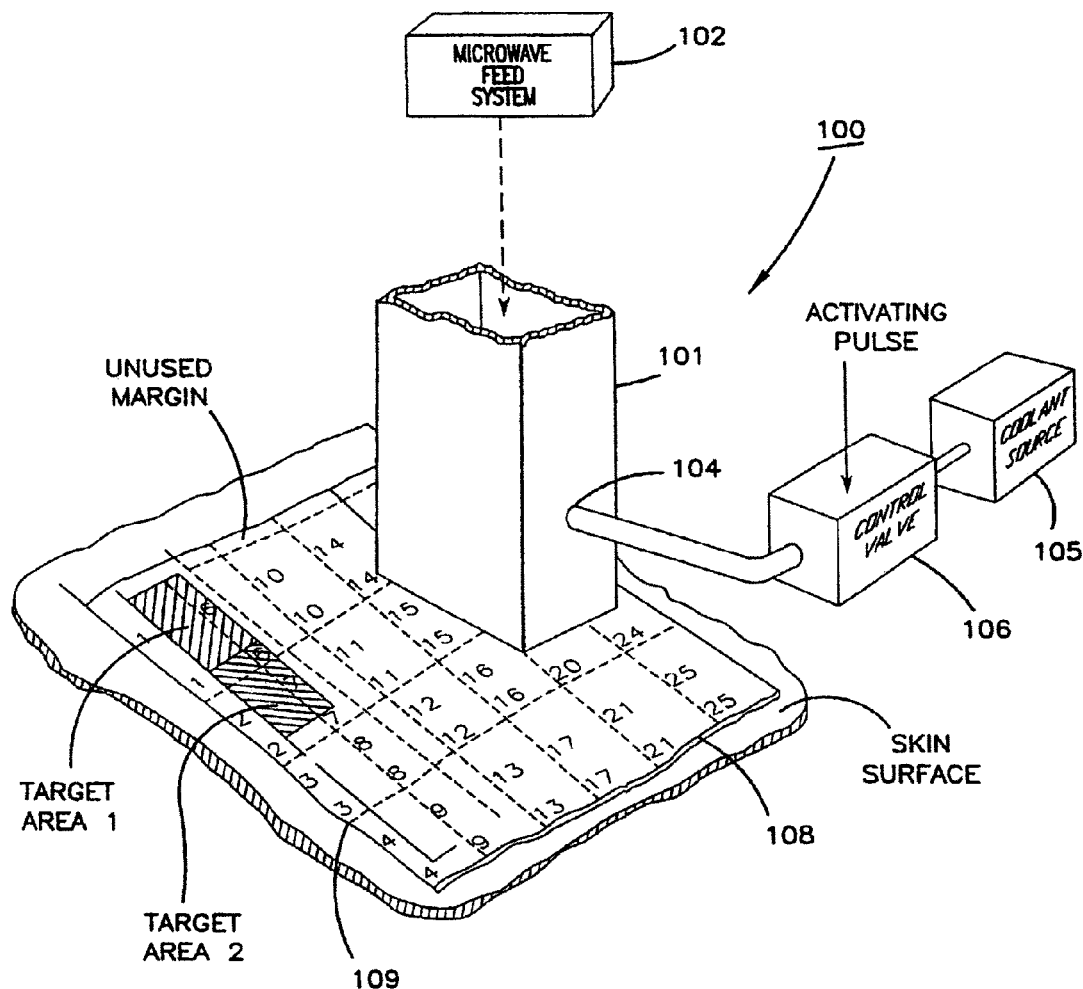
FIG. 10 is a simplified perspective view of a different microwave applicator used in conjunction with a removable positioning sheet.

An alternative applicator that covers a larger area and is employed with a peelable indicia label as shown in FIG. 10. The standard WR 62 waveguide for transmission of microwave energy at 14 GHz has, as previously mentioned, interior dimensions of 0.622"×0.311". An applicator 100 employing such a waveguide section 101 is used directly, without internal dielectric loading, to cover a substantially larger target area while employing air cooling. The waveguide section 101, coupled via a flexible waveguide and an impedance matching transition (not shown), if necessary, to a microwave feed system 102 has side wall ports 104 coupled to an external coolant source 105 which may deliver coolant through a control device 106 triggered, in relation to the microwave pulse, as previously described. Under some circumstances, when air is used as the coolant, it may simply be delivered continuously into the waveguide, the end of which can be blocked off by a microwave transmission window so that only the launching end and the skin surface are cooled. For use in a depilation procedure, the skin surface of a patient to be treated is covered with a sheet 108 having numbered guide indicia 109 for marking successive applicator 100 positions. These positions overlap because of the fact that the energy concentration is in the central region of the waveguide 101, at the normal maximum amplitude of the electric field in the $TE_{10}$ mode. The peel off label sheet 108 is covered on its skin-adhering side by a separable adhesive. Consequently, when the applicator 100 is moved between successive overlapping index positions marked 1,1,2,2 etc. at the side and corner of each position, the internal areas that are pathologically affected within each location are essentially contiguous, until the entire applicator 100 has been moved through all positions on the sheet 108, with dosages applied to all of the areas. Hair follicles having been destroyed in those areas, the procedure is terminated and the sheet 108 is peeled off, with the destroyed hair follicles and shafts adhering to it.

With the arrangement of FIG. 10, a longer microwave pulse duration or more wattage is needed for increasing the number of Joules because of the broader beam distribution, which means that, heating is at a slower rate (e.g., in the approximate proportion of 0.7° C. rise in skin temperature per joule for the large applicator versus 2.4° C. per joule for the dielectric filled smaller applicator). The skin temperature rise was reduced by a factor of 2 when using air at a temperature of between 0° C. and −5° C.

It should be noted, furthermore, that a standard open rectangular waveguide can be loaded with dielectric elements in a manner which enables size to be reduced without restricting coolant flow.

Another alternative that may be used, but is not shown in the figures, relates to a modification of the spacer element that is employed in the example of FIGS. 2 and 3. One can configure the spacer element with two alternative but adjacent positions for the applicator open (emitter) end, and arrange the applicator so that the emitter end can be shifted between the two positions. In a first or reserve position of the applicator, the target surface can be viewed through the spacer element, and positional adjustments can be made. This part of the spacer element is then used as a frame for visualizing the operative target on the skin surface when the applicator is in the reserve position. As soon as the target area is properly framed, the applicator is simply shifted from the reserve position to the operative position, in proper alignment with the target area, and the procedure can begin.

Figure 11:
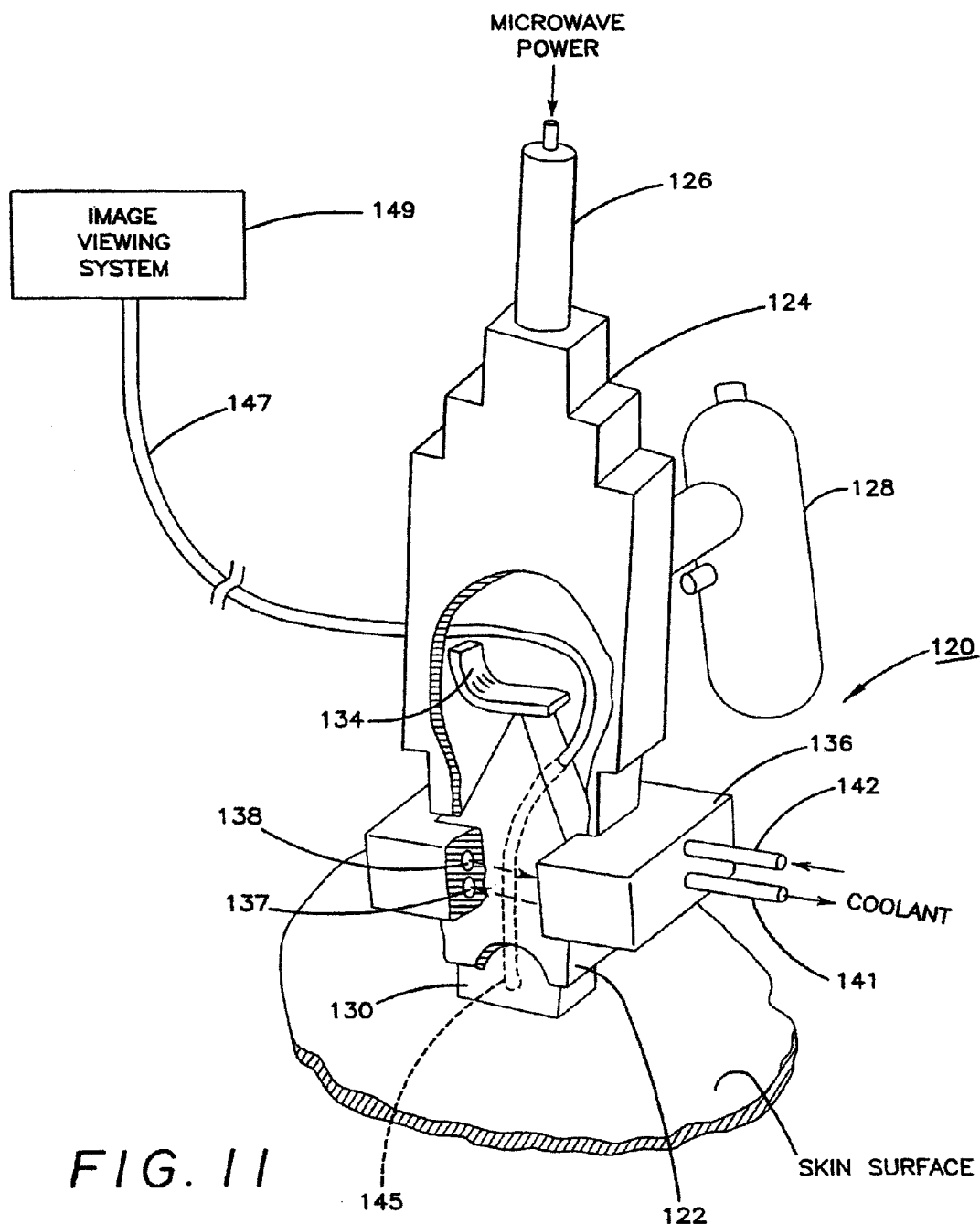
FIG. 11 is a perspective, partially broken away, view of an alternative applicator head including internal cooling and a viewing system.

A different approach to a useful applicator is shown in FIG. 11, to which reference is now made. This also illustrates a different means for cooling the skin surface, as well as for viewing the target area. In this example, the applicator 120 comprises an open-ended wave propagation segment 122 fed via a transition section 124 from a coaxial line 126. The unit may be physically manipulated by an attached handle 128. The open end of the waveguide 122 is filled by a dielectric element 130 which is not only of suitable electrical dielectric properties but a good heat conductor as well, such as boron nitride or beryllium oxide. The dielectric insert 130 extends beyond the open end of the waveguide, into contact with a skin surface that is to be exposed to microwave radiation. The interior end of the dielectric 130 is urged in the direction toward the skin surface by a non-conductive, non-absorptive microwave leaf spring 134 of selected force and compliance. Thus, the dielectric insert 130 presses on the skin surface with a yieldable force, selected to assure that contact is maintained but that any protruding veins or arteries are not closed simply by the force of the applicator 120. This applicator 120 and dielectric insert 130 are externally cooled by an encompassing sleeve 136 through which coolant is passed via internal conduits 137, 138 that communicate with an external supply (not shown) via external conduits 141, 142. Consequently, heat is extracted from the surface of the skin via the contacting dielectric 130 itself.

In addition, a target mark placed on the skin surface by the surgeon may be viewed by a system including a fiber optic line 145 that extends through the dielectric 130 and leads via a flexible fiber optic line 147 to an image viewing system 149.

In use, this applicator 120 of FIG. 11 covers a substantial chosen area, with the viewing and cooling features that simplify placement and minimize discomfort. The movable dielectric insert 130 can be a replaceable element, with different shapes of dielectrics being submitted where different conditions apply. It will be appreciated that other expedients may be utilized for shaping the microwave beam, including lens and diffuser systems.

Although a number of forms and modifications in accordance with the invention have been described, it will be appreciated that the invention is not limited thereto, but encompasses all forms and expedients in accordance with the appended claims.

TABLE 1

ANIMAL STUDY PROTOCOL NP970305
Applicator Tip: 0.250" × 0.150"; Cooling

| Rabbit | Dose (Joules) | Description of Skin | Histologic Description | | |
|---|---|---|---|---|---|
| | | | Tissue | Hair Follicles | Vasculature |
| B9 | 13 | skin intact; decreased density of hair | some fibrosis; mild edema | few hair follicles | vessels patent |
| B10 | 15.2 | skin intact; decreased density of hair | dermal fibrosis | relative absence of hair follicles | vessels patent |
| B11 | 19.6 | skin intact; decreased density of hair | normal | paucity of hair follicles | vessels patent |

TABLE 2

ANIMAL STUDY PROTOCOL NP970505
Applicator Tip: 0.250" × 0.150"; Cooling

| Rabbit | Dose (Joules) | Description of Skin | Histologic Description | | |
|---|---|---|---|---|---|
| | | | Tissue | Hair Follicles | Vasculature |
| B1/R | 22.4 | skin intact; hairless | tissue viable, dermal fibrosis | absent, squamous metaplasia | veins patent; arteries patent; increased intimal fibroblasts |
| B1/L | 22.4 | skin intact; hairless | tissue viable, dermal fibrosis | hair follicle destruction | veins patent, arteries patent, intimal fibrosis |
| B2/R | 20.0 | skin shiny; hairless | tissue viable, dermal fibrosis | hair follicle destruction | possible fibrous cord in small vein; arteries not seen in these sections |
| B2/L | 20.0 | skin intact, shiny and hairless | tissue viable, dermal fibrosis | hair follicle destruction | veins patent; arteries patent, increased intimal fibroblasts, mild edema |

TABLE 2-continued

ANIMAL STUDY PROTOCOL NP970505
Applicator Tip: 0.250" × 0.150"; Cooling

| Rabbit | Dose (Joules) | Description of Skin | Histologic Description | | |
|---|---|---|---|---|---|
| | | | Tissue | Hair Follicles | Vasculature |
| B3/R | 24.1 | skin shiny and hairless, fine granularity | tissue viable, dermal fibrosis, small area of necrosis on opposite side of ear (no cooling) | hair follicle destruction; squamous metaplasia | veins patent; arteries not seen in these sections |
| B3/L | 23.6 | three indurated areas, crusting of epidermis, hairless single punched out area | subacute granulation tissue | absence of hair follicles | vessels not seen in these sections |
| B4/R | 23.7 | skin shiny and hairless; fine granularity | tissue viable, dermal fibrosis | absence of hair follicles | fibrous cord in small vein; arteries not seen in these sections |
| B4/L | 23.6 | four indurated areas | tissue viable, dermal fibrosis | hair follicle destruction | congestion of small caliber veins; intimal fibrosis, narrowing of small arteries |
| B5/R | 20.7 | skin intact; hairless | tissue viable, dermal fibrosis | absence of hair follicles, squamous metaplasia | vein possibly narrowed; arteries patent, intimal fibrosis |
| B5/L | 21.4 | skin intact, hairless, tiny hole | tissue viable, dermal fibrosis | absence of hair follicles | veins patent; arteries patent, intimal fibrosis |
| B6/R | 22.0 | skin intact, hairless, fine granularity | tissue viable, dermal fibrosis | absence of hair follicles, squamous metaplasia | veins patent; narrowed small artery with intimal fibrosis |
| B6/L | 22.0 | punched out area | dermal fibrosis | hair follicle destruction, squamous metaplasia | arteries and veins patent |
| B7/R | 19.2 | skin intact, hairless | minimally affected | focal area of hair follicle destruction | veins patent; partial thrombois of small artery |
| B7/L | 20.5 | skin intact, hairless | dermal fibrosis | focal paucity of hair follicles, squamous metaplasia | veins patent; arteries patent, minimal intimal fibrosis |
| B8/R | 19.0 | skin intact, hairless | focal areas of dermal fibrosis | focal destruction of hair follicles | veins patent; occlusion of small artery with fibrous cord |
| B8/L | 21.4 | skin intact, hairless | dermal fibrosis, small zone of nodular fibrosis | destruction of hair follicles | veins patent; arteries not seen in these sections |
| B9/R | 23.0 | skin intact, hairless | small zone of dermal fibrosis | relative absence of hair follicles, squamous metaplasia | veins patent; arteries patent |

TABLE 2-continued

ANIMAL STUDY PROTOCOL NP970505
Applicator Tip: 0.250" × 0.150"; Cooling

| Rabbit | Dose (Joules) | Description of Skin | Histologic Description | | |
|---|---|---|---|---|---|
| | | | Tissue | Hair Follicles | Vasculature |
| B9/L | 23.0 | skin intact, hairless | dermal fibrosis | destruction of hair follicles, squamous metaplasia | veins patent; arteries patent with mild intimal fibrosis |
| B10/R | 24.6 | skin intact, hairless | mild fibrosis | destruction of hair follicles | veins patent; arteries patent with mild intimal fibrosis |
| B10/L | 24.7 | skin intact, hairless | dermal fibrosis | destruction of hair follicles | veins patent; partial thrombosis of small artery |
| B11/R | 22.4 | skin intact, hairless | minimal changes | minimal changes | veins patent; arteries patent |
| B11/L | 21.5 | skin intact, hairless | dermal fibrosis | destruction of hair follicles, squamous metaplasia | veins patent; arteries patent |
| B12/R | 20.6 | skin intact, hairless | dermal fibrosis | destruction of hair follicles, squamous metaplasia, remnants of follicles seen | veins patent; arteries patent |
| B12/L | 19.6 | skin intact, hairless | zone of dermal fibrosis | destruction of hair follicles | veins patent; arteries patent |

TABLE 3

ANIMAL STUDY PROTOCOL NP970603
Applicator Tip: 0.250" × 0.150"

| Rabbit | Pigmented | Dose (Joules) | Cooling | Appearance of Skin |
|---|---|---|---|---|
| A1 | No | 5.3 | No | skin intact - back and ear |
| | | | Yes | skin intact - back and ear |
| A2 | Yes | 5.6 | No | skin intact - back and ear |
| | | | Yes | skin intact - back; tiny dot left ear |
| B1 | No | 9.4 | No | back - minimal pallor ⅔ sites; skin on ear intact |
| | | | Yes | skin intact - back and ears |
| B2 | Yes | 9.3 | No | skin on back obscured by hair growth; skin on ear intact |
| | | | Yes | skin on back obscured by hair growth; skin on ear intact |
| C1 | No | 14.3 | No | back - slight abrasion ⅔ sites, small scab 3; skin on ear intact |
| | | | Yes | skin intact - back and ear |
| C2 | Yes | 14.8 | No | skin on back obscured by hair growth; skin on ear intact |
| | | | Yes | skin on back obscured by hair growth; skin on ear intact |
| D1 | No | 18.4 | No | back - scabs all 3 sites; ear - tiny scab |
| | | | Yes | back - slight pallor ⅔ sites, minimal change at site 3; ear - minimal change |
| D2 | Yes | 18.6 | No | back - small, raised areas at all 3 sites; ear - small raised area |
| | | | Yes | skin intact - back and ear |

TABLE 4

ANIMAL STUDY PROTOCOL NP970208
No Cooling

| Rabbit | Joules | Histology-Tissue | Histology-Vein | Histology-Artery | Clinical-Tissue | Clinical-Vessels |
|---|---|---|---|---|---|---|
| D1/R | 10.4 | Viable, dermal fibrosis | Patent | Narrowed | Intact | Vein sl. Purple |
| D1/L | 10.4 | Viable, dermal edema | Partial occlusion | >occlusion than vein | Intact | Narrowing |

TABLE 4-continued

ANIMAL STUDY PROTOCOL NP970208
No Cooling

| Rabbit | Joules | Histology-Tissue | Histology-Vein | Histology-Artery | Clinical-Tissue | Clinical-Vessels |
|---|---|---|---|---|---|---|
| D2/R | 10.4 | Viable, dermal fibrosis | Sl. altered, but patent | Sl. altered, but patent | Small area of blanching | Patent, sl. darkening |
| D2/L | 10.4 | Viable, dermal fibrosis | Patent | Tiny, vessel collapsed | Small area of blanching | Patent, sl. darkening |
| C1/R | 12.0 | Viable, dermal fibrosis | Micro-thrombosis | Patent | Sl. blanching | Vein segmentally narrowed |
| C1/L | 12.0 | Viable, dermal fibrosis | Ghosted, without endothelium, but patent. Venular congestion | Narrowed and focally thrombosed | Sl. blanching | Vein narrowed segmentally |
| C2/R | 12.0 | Viable, dermal fibrosis | Organization with evidence of recanalization | Not described | Mild blanching | Vein narrowed segmentally |
| C2/L | 11.6 | Viable, dermal fibrosis | Thrombosis with organization | Not described | Mild blanching | Vein narrowed segmentally |
| B1/R | 14.0 | Viable, dermal fibrosis | Patent; not well seen in areas of fibrosis | Not well visualized | Mild blanching | Vessel seen |
| B1/L | 13.7 | Viable, dermal fibrosis | Ghosted, necrotic, contains blood | Patent | Mild blanching | Vessel seen |
| B2/R | 14.0 | Viable, dermal fibrosis | Patent | Lumina narrowed by intimal hyperplasia | Mild blanching | Vessel seen |
| B2/L | 13.6 | Viable, dermal fibrosis | Occlusion focally | Not described | Minimal changes | Vein narrowed segmentally |
| A7/R | 16.0 | Viable, dermal fibrosis | Focally occluded | Focally occluded | Minimal changes | Mild blushing around vein |
| A7/L | 16.3 | Viable, dermal fibrosis | Partial occlusion, congestion of venules | >occlusion than vein | Mild induration | Blushing around vein |
| A6/R | 15.5 | Viable, dermal fibrosis | Patent | Focal occlusion | Minimal changes | Veins seen |
| A6/L | 15.5 | Viable, dermal fibrosis | Focally absent | Focally absent | Mild blanching | Vein segmentally narrowed |
| A5/R | 17.4 | Viable, dermal fibrosis | Thrombosis with organization | Thrombosis with organization | Mild blanching | Vein narrowed |
| A5/L | 17.5 | Viable, scale crust present, dermal fibrosis | Occlusion (organization) | Not described | Mild to moderate induration | Vein narrowed |

What is claimed is:

1. A handheld applicator configured to direct therapeutic microwave energy toward an epidermal surface, comprising:
   a housing having a distal end adapted to be placed on a skin surface;
   a microwave waveguide disposed in the housing and radiating towards the distal end of the housing, the microwave waveguide being positioned within the housing so as to be set off from the skin surface when the distal end of the housing is placed on the skin surface;
   a dielectric element disposed in the housing and extending beyond the microwave waveguide, the dielectric element being configured to spread an electric field distribution of delivered microwave energy exiting the microwave waveguide wherein at least a portion of the dielectric element is arranged to contact the skin surface and wherein the dielectric element is adapted to improve an impedance match between the applicator and the skin surface;
   a coolant source disposed in the housing and configured to dispense a coolant to cool the skin surface; and
   a temperature sensor disposed and configured to sense a temperature change at the skin surface.

2. A handheld applicator configured to direct therapeutic microwave energy toward an epidermal surface, comprising:

a housing having a distal end adapted to be placed on a skin surface;

a microwave waveguide disposed in the housing, the microwave waveguide configured to deliver microwave energy and being positioned within the housing so as to be set off from the skin surface when the distal end of the housing is placed on the skin surface;

a dielectric element disposed in the housing and configured to spread an electric field distribution of delivered microwave energy radiated by the microwave waveguide, wherein at least a portion of the dielectric element is arranged to contact the skin surface and wherein the dielectric element is adapted to improve an impedance match between the applicator and the skin surface;

a coolant source disposed in the housing and configured to dispense a coolant to cool the skin surface; and a temperature sensor the housing and configured to sense a temperature change at the skin surface.

* * * * *